(12) United States Patent
Li et al.

(10) Patent No.: US 11,774,425 B1
(45) Date of Patent: Oct. 3, 2023

(54) FLEXIBLE HYDROGEN SENSOR WITH ULTRA-HIGH SENSITIVITY AND WIDE RANGE AND FABRICATION METHOD THEREFOR

(71) Applicant: NANJING UNIVERSITY, Jiangsu (CN)

(72) Inventors: Aidong Li, Jiangsu (CN); Qiang Ren, Jiangsu (CN); Jian Chen, Jiangsu (CN); Jiabin Fang, Jiangsu (CN); Min Han, Jiangsu (CN)

(73) Assignee: NANJING UNIVERSITY, Jiangsu (CN)

( * ) Notice: Subject to any disclaimer, the term of this patent is extended or adjusted under 35 U.S.C. 154(b) by 0 days.

(21) Appl. No.: 18/033,072

(22) PCT Filed: May 13, 2021

(86) PCT No.: PCT/CN2021/093518
§ 371 (c)(1),
(2) Date: Apr. 21, 2023

(87) PCT Pub. No.: WO2022/127012
PCT Pub. Date: Jun. 23, 2022

(30) Foreign Application Priority Data

Dec. 14, 2020 (CN) .......................... 202011472415.0

(51) Int. Cl.
*G01N 33/00* (2006.01)
*C23C 16/455* (2006.01)
*B82B 3/00* (2006.01)

(52) U.S. Cl.
CPC ......... *G01N 33/005* (2013.01); *B82B 3/0023* (2013.01); *C23C 16/45555* (2013.01)

(58) Field of Classification Search
CPC ................ G01N 33/005; B82B 3/0023; C23C 16/45555
See application file for complete search history.

(56) References Cited

U.S. PATENT DOCUMENTS

2013/0202489 A1\* 8/2013 Ong ..................... G01N 33/005
977/902

FOREIGN PATENT DOCUMENTS

| CN | 107144600 | 9/2017 |
| CN | 112505107 | 3/2021 |

(Continued)

OTHER PUBLICATIONS

"Dense Palladium Nanoparticle Arrays with Controlled Coverage for Fast Hydrogen Sensor", Proceedings of the 2011 6th IEEE International Conference on Nano/Micro Engineered and Molecular Systems Feb. 20-23, 2011, Kaohsiung, Taiwan (Year: 2011 ).\*

(Continued)

*Primary Examiner* — Nathaniel J Kolb
(74) *Attorney, Agent, or Firm* — JCIPRNET

(57) ABSTRACT

Disclosed is a flexible hydrogen sensor with ultra-high sensitivity and a wide range and a fabrication method therefor. The sensor includes a conductive electrode layer (4), a sensing layer and a flexible substrate layer (1) in sequence from top to bottom. The sensing layer includes a $MO_x$ film (2) and Pd nanoparticles (NPs) (3), and the Pd NPs (3) are covered on the $MO_x$ film (2). A traditional metal oxide type hydrogen sensor and a quantum conductance-based hydrogen sensor are combined on a flexible polymer substrate by means of an atomic layer deposition (ALD) technology and a cluster beam deposition (CBD) technology, so as to obtain a flexible hydrogen sensor with ultra-high sensitivity, a wide range and excellent selectivity and lower working temperature.

5 Claims, 7 Drawing Sheets

(56) References Cited

FOREIGN PATENT DOCUMENTS

| JP | 4602000 | 12/2010 |
|---|---|---|
| KR | 20150000737 | 1/2015 |
| KR | 20190122489 | 10/2019 |

OTHER PUBLICATIONS

"Flexible and Highly Sensitive Hydrogen Sensor Based on Organic Nanofibers Decorated by Pd Nanoparticles", Sensors Mar. 14, 2019; 19, 1290 (Year: 2019).*
S H Wu et al., "Flexible hydrogen sensor based on Pd/TiO2 nanofilm with fast response", The 6th Global Conference on Polymer and Composite Materials, Jul. 31, 2019, pp. 1-7.
Jae-Hun Kim et al., "Hydrogen sensing characteristics of Pd-decorated ultrathin ZnO nanosheets", Sensors and Actuators B: Chemical, Nov. 23, 2020, pp. 1-11.
Jiwon Lee et al., "A hydrogen gas sensor employing vertically aligned TiO2 nanotube arrays prepared by template- assisted method", Sensors and Actuators B: Chemical, Aug. 6, 2011, pp. 1494-1498.
Shen Linwu et al., "A Flexible Hydrogen Sensor Based on Electron Tunneling Mechanism", Chinese Journal of Sensors and Actuators, with English abstract, Feb. 29, 2020, pp. 186-193.
"International Search Report (Form PCT/ISA/210) of PCT/CN2021/093518," dated Sep. 13, 2021, with English translation thereof, pp. 1-6.

* cited by examiner

FLEXIBLE HYDROGEN SENSOR WITH ULTRA-HIGH SENSITIVITY AND WIDE RANGE AND FABRICATION METHOD THEREFOR

CROSS-REFERENCE TO RELATED APPLICATION

This application is a 371 of international application of PCT application serial no. PCT/CN2021/093518, filed on May 13, 2021, which claims the priority benefit of China application no. 202011472415.0, filed on Dec. 14, 2020. The entirety of each of the above mentioned patent applications is hereby incorporated by reference herein and made a part of this specification.

TECHNICAL FIELD

The disclosure belongs to the field of hydrogen sensors, and particularly relates to a flexible hydrogen sensor with ultra-high sensitivity and a wide range and a fabrication method therefor.

BACKGROUND ART

As a gas with the lightest density, hydrogen has important value in industrial synthesis, petrochemical hydrogenation, dehydrogenation and application as a reducing agent. As a clean and renewable secondary energy, the hydrogen energy will play an important role in the field of new energy in the future, especially fuel cells and power vehicles. However, hydrogen is colorless and odorless and has the danger of explosion when the concentration of hydrogen in the air is 4-75 vol %, which greatly limits the production, storage, transportation and use of hydrogen. It is an urgent task to develop a safe and reliable hydrogen sensor with high sensitivity/selectivity and easy use.

As a common hydrogen sensor, a metal oxide semiconductor resistive hydrogen sensor has the advantages of high sensitivity, good stability, low cost, and the like, but has poor selectivity and a higher operating temperature (generally about 300° C.). Moreover, at a low temperature or a room temperature, the metal oxide semiconductor resistive hydrogen sensor has low sensitivity and slow response and cannot work normally. For example, common $SnO_2$ and ZnO gas-sensing materials have such intractable problems. In addition to the metal oxide semiconductor resistive hydrogen sensor, a quantum conductance-based new resistive hydrogen sensor has also drawn great attention in recent years. By using precious metal Pd nanowires or nanoparticles (NPs) as sensing media, such sensors have the characteristics of fast response and excellent selectivity, but have a narrower range, low sensitivity and poor stability. In addition, with the continuous development of the Internet of Things, the demand for flexible devices is also increasing rapidly. It is very important for the flexible electronics to develop flexible hydrogen sensors to replace traditional rigid hydrogen sensors.

Atomic layer disposition (ALD) and cluster beam deposition (CBD) are new material fabrication technologies with vigorous development. The ALD is a method for forming a film by alternately introducing volatile precursor pulses into a reactor and conducting a chemical adsorption reaction on the surface of a deposited substrate. The unique self-limiting and self-saturating reaction mechanism of the ALD ensures the large-area uniformity and excellent three-dimensional conformality of a deposited film and the accurate controllability of a film thickness (angstrom scale). In recent years, the ALD has broad application prospects in the fields of microelectronics, optoelectronics, nanotechnology, new energy, catalysis, biomedicine, and the like. However, the application of the ALD technology in the field of hydrogen sensors is relatively few. Especially, the research on the ALD fabrication of flexible hydrogen sensors with ultra-high sensitivity is extremely scarce. In the CBD technology, clusters are formed through a gas phase aggregation process, and a cluster beam is formed by the expansion of an aerodynamic nozzle and then deposited on a substrate at a sound velocity or after being accelerated in vacuum. The CBD technology can accurately control the size and distribution of NPs, and can obtain NP arrays with controllable size/coverage, high purity, and uniform particle distribution. The CBD technology has shown great technical advantages in the field of quantum conductance-based hydrogen sensors, and is expected to develop into a large-scale fabrication technology of nanostructures based on NPs commonly used in the industry.

SUMMARY OF INVENTION

The disclosure provides a flexible hydrogen sensor with ultra-high sensitivity and a wide range and a fabrication method therefor, and obtains a flexible hydrogen sensor with ultra-high sensitivity, a wide range and low working temperature, thereby solving the disadvantages of low sensitivity, narrow detection range, poor selectivity, high working temperature, and the like of a hydrogen sensor.

In order to achieve the above objectives, the disclosure adopts the following technical solutions:

A flexible hydrogen sensor with ultra-high sensitivity and a wide range includes a conductive electrode layer, a sensing layer and a flexible substrate in sequence from top to bottom, wherein the sensing layer includes a $MO_x$ film and Pd nanoparticles (NPs), and the Pd NPs are covered on the $MO_x$ film.

In the above structure, the flexible substrate is a flexible polymer substrate, and the flexible polymer substrate includes, but is not limited to, polyimide (PI), polyethylene terephthalate (PET), polyaniline (PANI), polyethylene naphthalate (PEN), polyether ether ketone (PEEK), polyphenylene sulfide (PPS), polymethyl methacrylate (PMMA), polydimethylsiloxane (PDMS), polycarbonate (PC), and cellophane;

the conductive electrode layer is a metal interdigital electrode, the length of the metal interdigital electrode is 5-6 mm, the width is 4-5 mm. The interdigital electrode consists of 12 pads, whose length and width are 1-2 mm and 200 m, respectively. The distance between two pads is also 100-200 μm, and the material of the metal interdigital electrode is a metal such as gold, silver, platinum or aluminum with a thickness of about 100-200 nm; and the thickness of the $MO_x$ film is 5-50 nm, the M is Sn, Zn, Ti, Ta, Hf or Zr, the coverage rate of the Pd NPs on the $MO_x$ film is 5-50%, and the coverage rate refers to an occupied area of Pd NPs per unit area.

A method for fabricating a flexible hydrogen sensor with ultra-high sensitivity and a wide range includes the following steps:
  (1) ultrasonically cleaning a flexible polymer substrate with isopropanol, ethanol and deionized water in sequence for 5-10 min, and blow-drying the flexible polymer substrate with high-purity nitrogen (99.999%) for later use;

(2) depositing a layer of $MO_x$ film with a thickness of 5-50 nm at a low temperature by thermal atomic layer deposition (ALD) or plasma-enhanced ALD (PEALD) on the flexible polymer substrate treated in step (1);

(3) depositing Pd NPs with a coverage rate of 10-50% on the $MO_x$ film grown in step (2) by a cluster beam deposition (CBD) technology;

(4) depositing a metal interdigital electrode with a thickness of 100-200 nm on the $MO_x$ film with Pd NPs in step (3) as a conductive electrode by a mask, and performing wiring and packaging to obtain a $MO_x$-based flexible hydrogen sensor loaded with Pd NPs.

In the above steps, the low-temperature deposition temperature of ALD in step (2) is from a room temperature to 350° C.;

the parameters of the CBD in step (3) are as follows: the pressure of a chamber is $10^{-5}$ Pa, a cluster source is filled with 100 Pa argon during deposition, the sputtering power is 20-50 W, the condensation distance is 30-80 mm, and the purity of the metal Pd target used is 99.9999%; and in step (4), the conductive electrode is prepared by means of magnetron sputtering, vacuum evaporation or electron beam thermal evaporation.

Beneficial effects: The examples of the disclosure provide a flexible hydrogen sensor with ultra-high sensitivity and a wide range and a fabrication method therefor. Pd NPs are deposited after a $MO_x$ film is grown on a flexible polymer substrate. A fabrication process is compatible with a semiconductor process so as to be suitable for large-scale production. The fabricated hydrogen sensor has excellent hydrogen sensor properties, a sub-ppm (parts per million)-level low detection concentration, an ultra-wide detection range, and ultra-high hydrogen selectivity. Since the flexible polymer substrate is bendable, the hydrogen sensor based on the flexible polymer substrate has broad n prospects in the field of flexible sensors.

BRIEF DESCRIPTION OF DRAWINGS

FIG. 7 illustrated in (b) shows a stability curve of a Pd NPs/$SnO_2$ sample to 30 ppm $H_2$ at an operating temperature of 125° C. in an example of the disclosure.

DESCRIPTION OF EMBODIMENTS

Example 1

Figure 1:
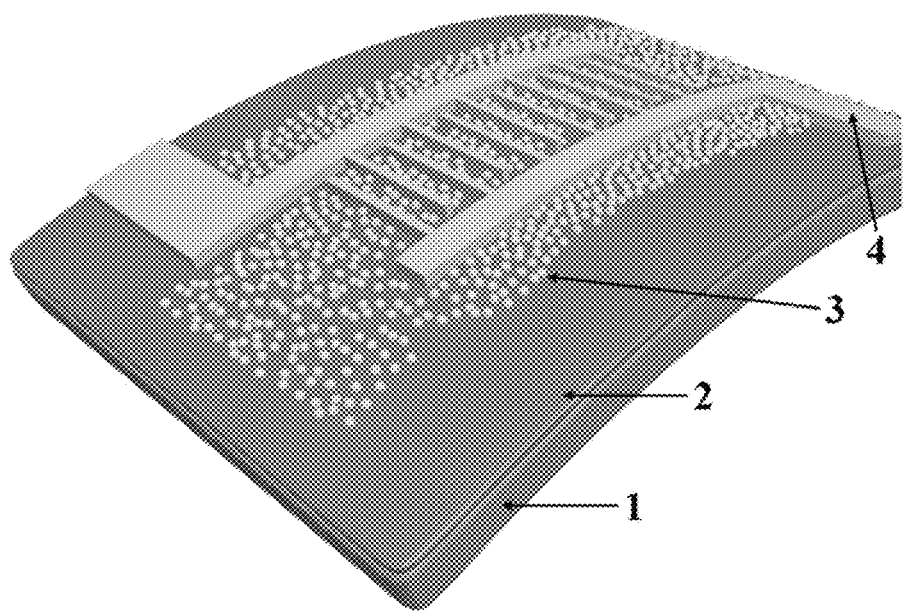
FIG. 1 shows a schematic structural diagram of a flexible hydrogen sensor with ultra-high sensitivity in an example, wherein 1 denotes a flexible substrate, 2 denotes a $MO_x$ film deposited by ALD, 3 denotes Pd NPs deposited by CBD, and 4 denotes an interdigital conductive electrode.
Figure 2:
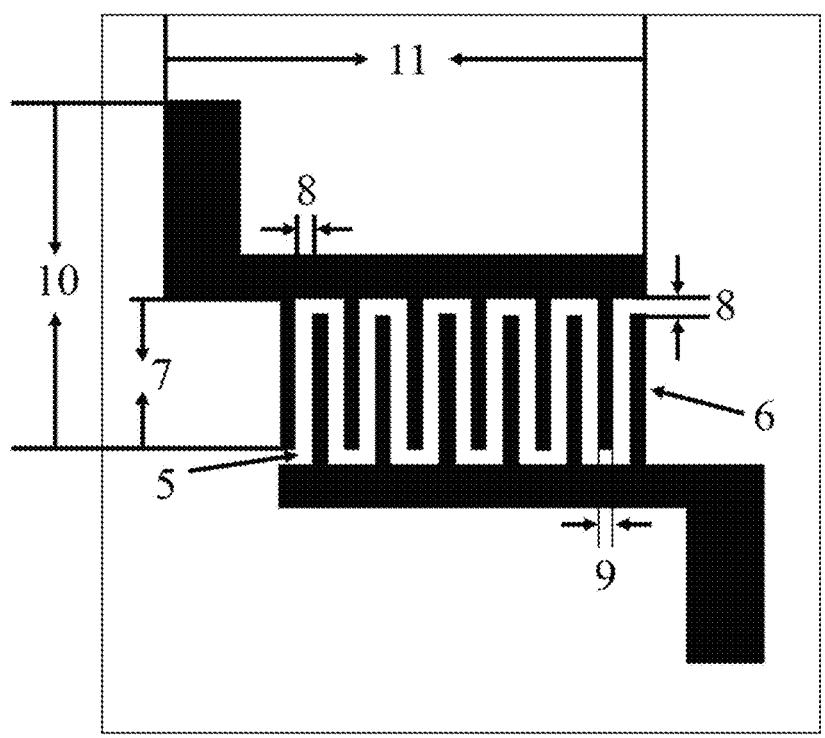
FIG. 2 shows a schematic diagram of a mask of an interdigital electrode in an example, wherein 5 (white part) denotes a metal material of the mask, 6 (black part) denotes a gap of the mask, 7 denotes a pad length of the interdigital electrode, 8 denotes a gap length of interdigital electrode pad, 9 denotes a pad width of the interdigital electrode, 10 denotes a width of the interdigital electrode, and 11 denotes a length of the interdigital electrode.

As shown in FIG. 1, a hydrogen sensor with ultra-high sensitivity based on a flexible polymer substrate includes a flexible polymer PI substrate, a $MO_x$ (M=Sn, X=2) film, Pd NPs and a platinum interdigital electrode, and specifically includes a platinum interdigital electrode, Pd NPs, an $SnO_2$ film and a PI substrate in sequence from top to bottom, wherein the coverage rate of the Pd NPs on the $SnO_2$ film is 20%.

Figure 3:
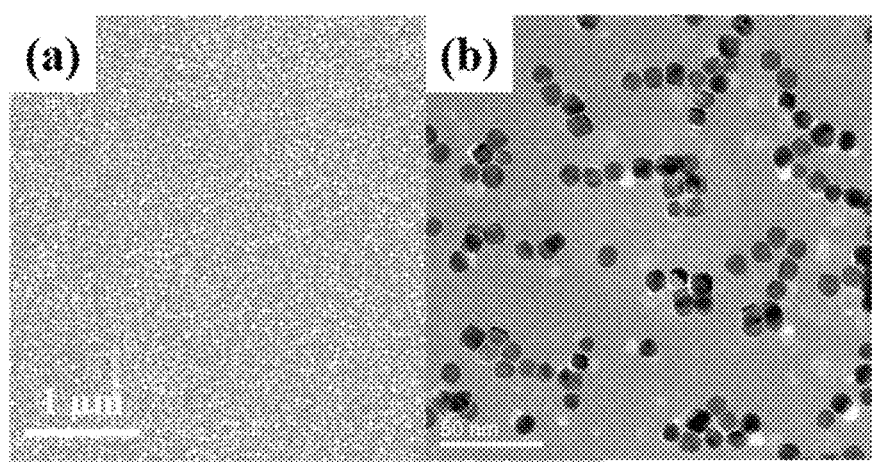
FIG. 3 shows a scanning electron microscope (SEM) image (a) and a transmission electron microscope (TEM) image (b) of a Pd NPs/$SnO_2$ sample in an example.

A method for fabricating the above sensor includes the following steps:

(1) as shown in FIG. 1, the PI was selected as a substrate of the sensor and put on a cleaning rack, the cleaning rack was put in a beaker, then, the PI substrate was ultrasonically cleaned with isopropanol, ethanol and deionized water respectively for 5 min, and finally, the cleaned PI substrate was blow-dried with high-purity nitrogen (99.999%) for later use;

(2) a layer of ultra-thin $SnO_2$ film was deposited on the PI substrate cleaned in step (1) by thermal ALD at a deposition temperature of 120° C., the precursor sources used were tetra(dimethylamino)tin and deionized water, the pulse time and cleaning time of both the tetra(dimethylamino)tin source and deionized water source were 0.2 s and 6 s respectively, the cycle number of deposition was 140, and test results of an ellipsometer show that the growth rate was 0.1 nm/cycle;

(3) on the basis of step (2), Pd NPs with a coverage rate of 20% were deposited by a CBD technology, wherein during deposition, the sputtering power was 40 W, the condensation distance was 60 mm, and the content of the Pd NPs was controlled by adjusting the deposition time; as shown in FIG. 3, the deposited Pd NPs were uniformly distributed, independent of each other and free from aggregation, and the diameter of the NPs was 8-10 nm; and (4) an interdigital electrode mask was closely attached to the sample obtained after step (3) was completed, a platinum metal with a thickness of about 150 nm was sputtered as a conductive electrode by means of magnetron sputtering, and wiring and packaging were performed to serve as a flexible sensing element for detecting hydrogen.

Figure 4:
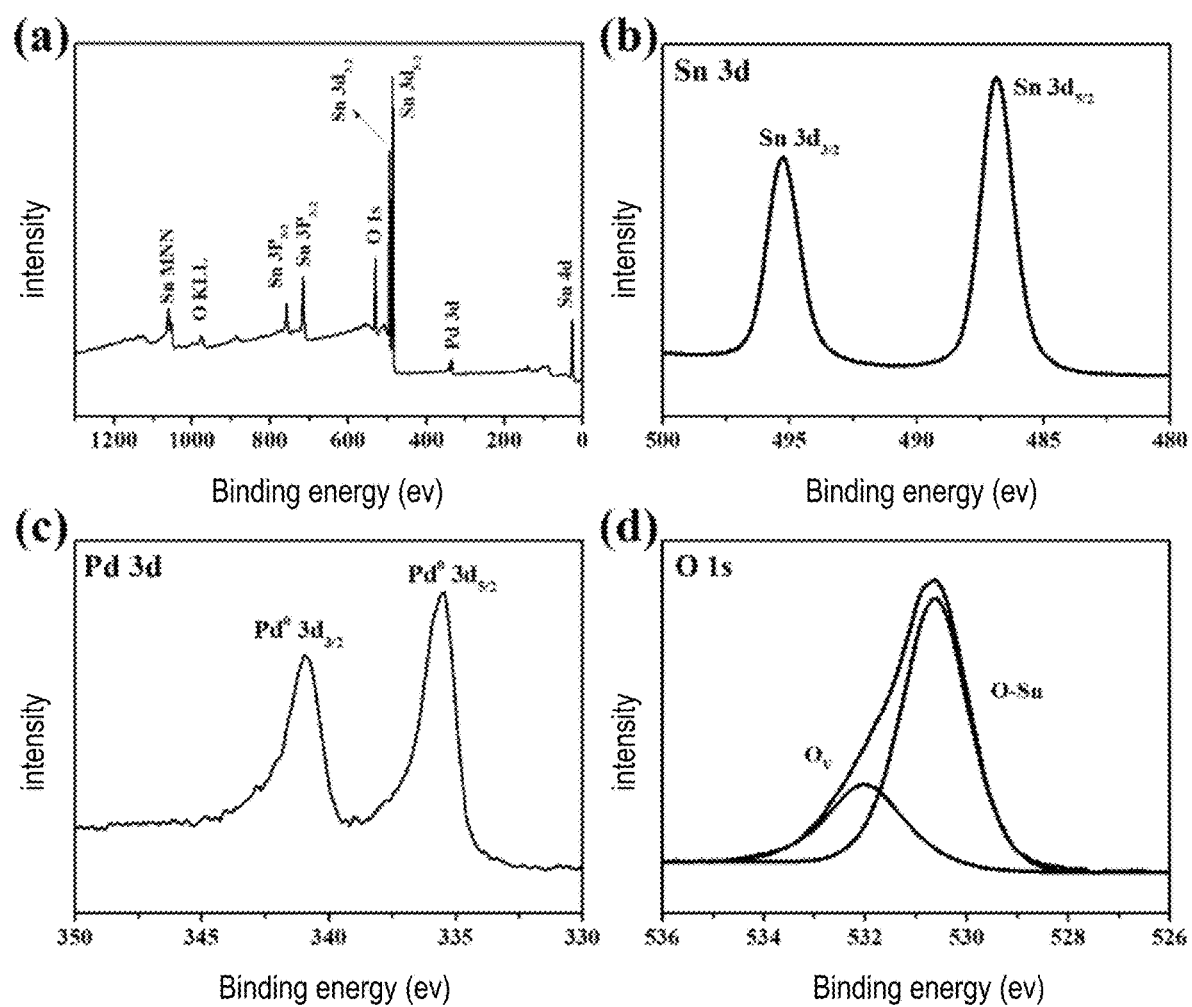
FIG. 4 shows XPS spectra of a Pd NPs/$SnO_2$ sample in an example: (a) wide-scan, (b) Sn 3d, (c) O 1s, and (d) Pd 3d.

FIG. 4 shows XPS photoelectron spectra of Pd NPs/$SnO_2$. It can be seen from the figure that the surface of the sample contains Sn, O and Pd elements, wherein Sn is $Sn^{4+}$, and Pd is metallic Pd. This indicates that an $SnO_2$ film is prepared by ALD, and Pd metal NPs are deposited by a CBD technology.

Figure 5:
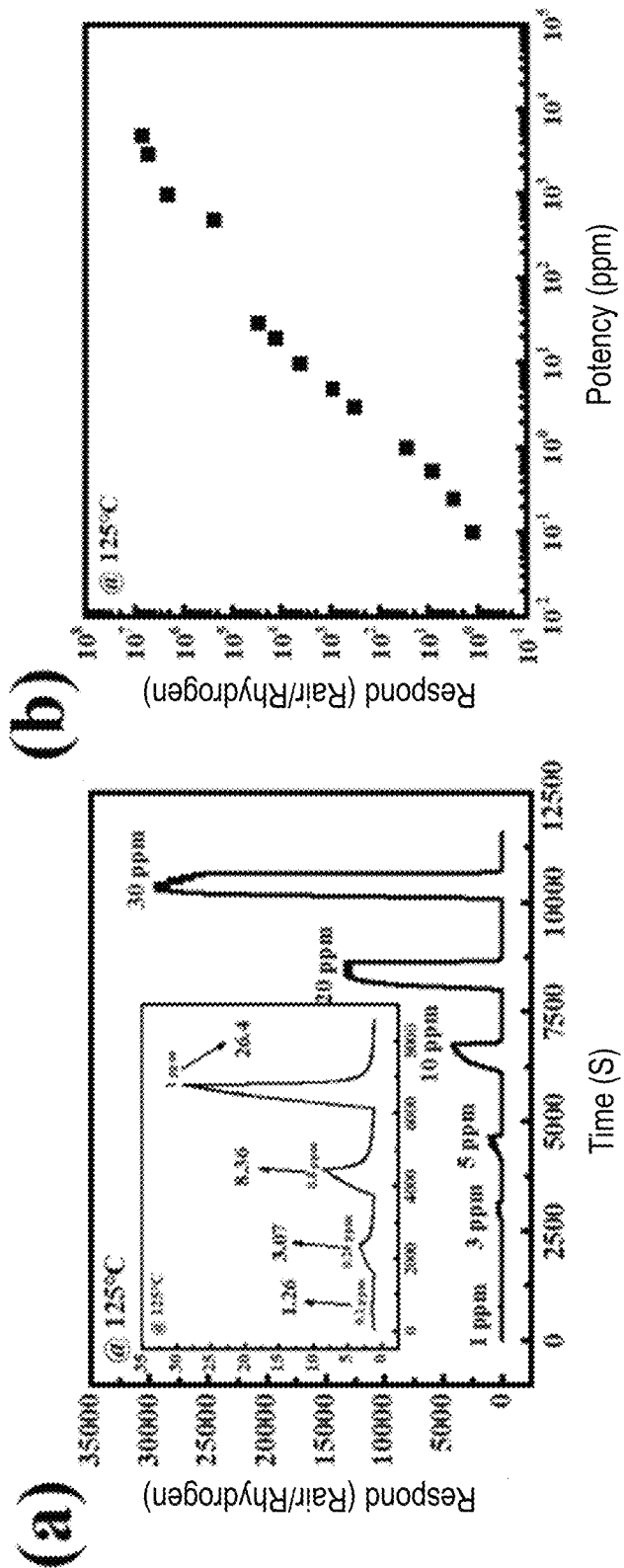
FIG. 5 shows a response curve of a Pd NPs/$SnO_2$ sample to various hydrogen concentrations at an operating temperature of 125° C. in an example.

FIG. 5 shows response curves of a Pd NPs/$SnO_2$ hydrogen sensor sample by introducing $H_2$ with different concentrations at an operating temperature of 125° C. It can be seen that the hydrogen sensor has ultra-high sensitivity, the response of the hydrogen sensor reaches up to about 30000 when 30 ppm of $H_2$ is introduced, and the response of the hydrogen sensor reaches up to $10^7$ orders of magnitude when 5000 ppm of $H_2$ is introduced. As shown in FIG. 5(b), the hydrogen sensor has strong response in the range of 0.1-10000 ppm of $H_2$. It can be seen that the hydrogen sensor has an ultra-low limit of detection, an ultra-wide detection range, and a higher detection resolution.

Figure 6:
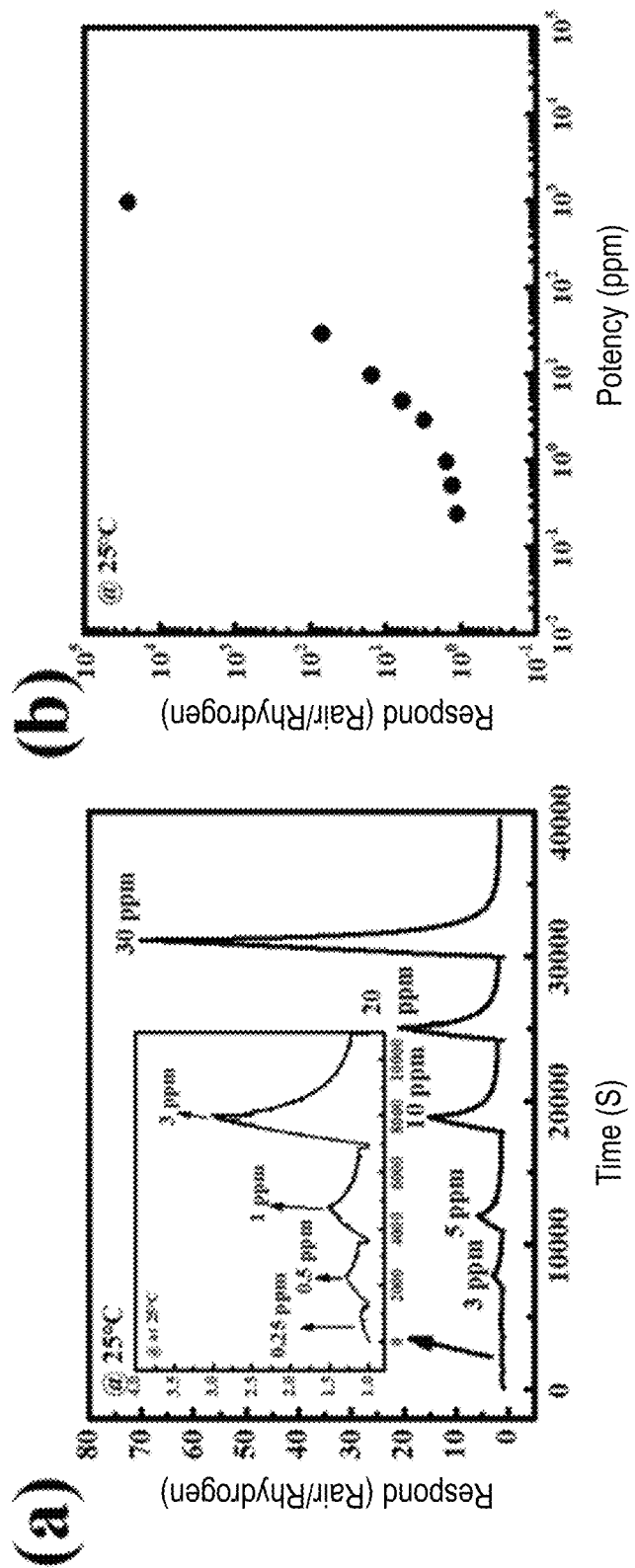
FIG. 6 shows a response curve of a Pd NPs/$SnO_2$ sample to various hydrogen concentrations at an operating temperature of 25° C. in an example.

FIG. 6 shows response properties of a Pd NPs/$SnO_2$ hydrogen sensor sample to $H_2$ with different concentrations at a room temperature. Room temperature detection is very helpful to reduce the energy consumption and improve the safety of the hydrogen sensor. Although the properties are reduced compared with those at 125° C., there is still a clear response curve to $H_2$ with different concentrations. The sensor still has resistance response of $10^4$ orders of magnitude to 5000 ppm of $H_2$, and the lowest limit of detection can also be as low as 0.25 ppm. It can be seen that the hydrogen sensor has excellent room temperature detection properties.

Figure 7:
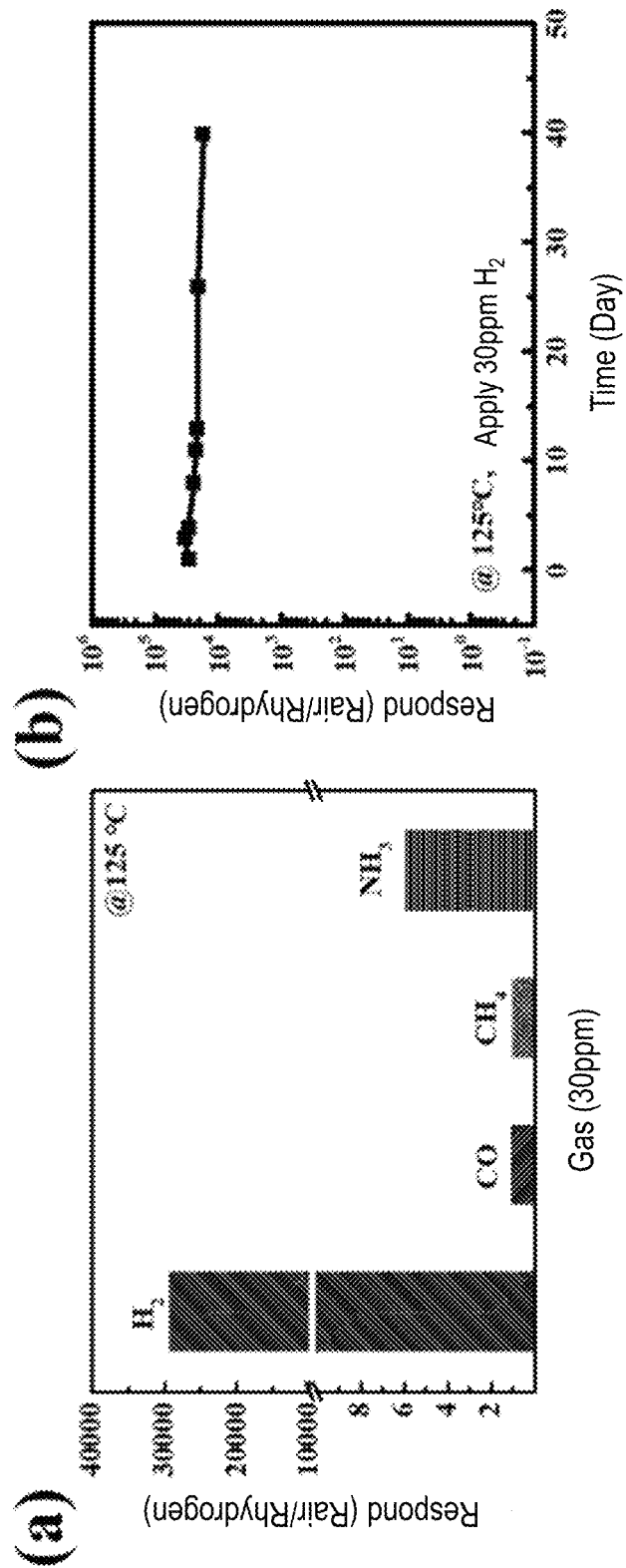
FIG. 7 illustrated in (a) shows sensitivity of a Pd NPs/$SnO_2$ sample to 30 ppm $H_2$, CO, $CH_4$ and $NH_3$ at an operating temperature of 125° C. in an example.

FIG. 7 illustrated in (a) shows comparison diagrams of selectivity and stability of a Pd NPs/$SnO_2$ hydrogen sensor. It can be seen from (a) of FIG. 7 that after $H_2$, CO, $CH_4$ and $NH_3$ with the same concentration of 30 ppm are introduced respectively, the sensor has almost no response to CO and $CH_4$, the sensitivity of the sensor to $NH_3$ is about 6, and the response of the sensor to $H_2$ reaches up to about 30000, so the sensor has super hydrogen selectivity. FIG. 7 illustrated in (b) shows hydrogen response properties of the sensor tested at different interval days, indicating that the sensor has better stability. The hydrogen sensing property of the hydrogen sensor is reduced with the increase of the storage time. However, at 125° C., the hydrogen sensor still has resistance response of $10^4$ orders of magnitude to 30 ppm of $H_2$, reflecting that the hydrogen sensor has better stability.

Figure 8:
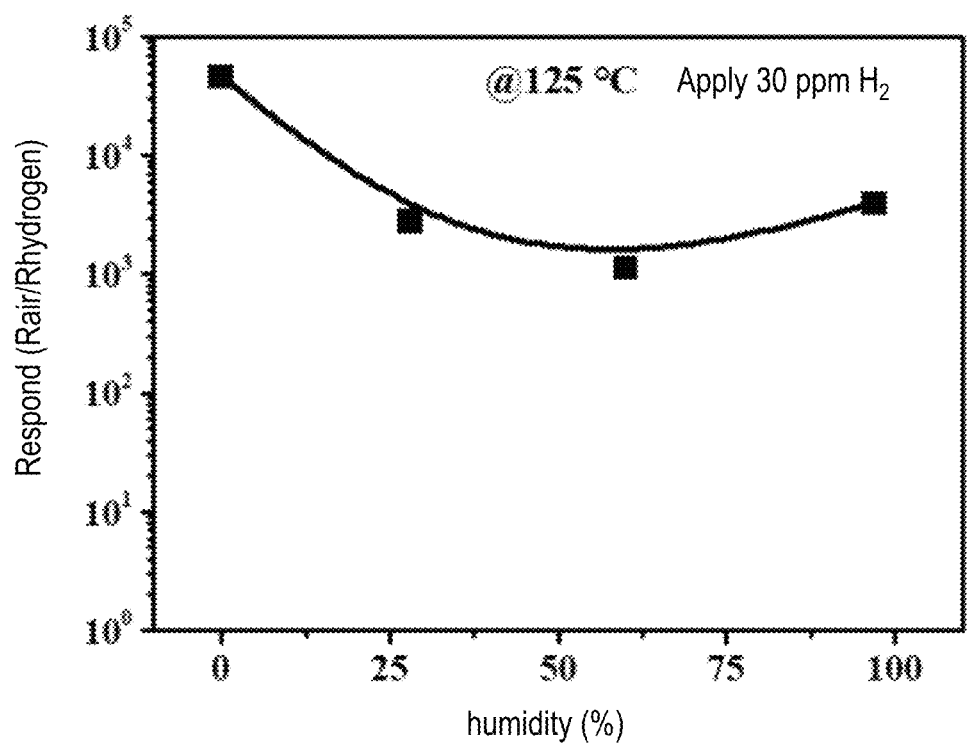
FIG. 8 shows a sensitivity change curve of a Pd NPs/$SnO_2$ flexible hydrogen sensor under various relative humidities in an example, wherein an operating temperature is 125° C., and an $H_2$ concentration is 30 ppm.

FIG. 8 shows sensitivity change conditions of a Pd NPs/$SnO_2$ flexible hydrogen sensor to 30 ppm of $H_2$ under different relative humidities at 125° C. With the increase of the air humidity, the sensitivity property of the flexible hydrogen sensor is reduced to a certain extent, but is still maintained at $10^3$ orders of magnitude. Especially, in a case that the humidity of the sensor is 97% of RH, the hydrogen response of the sensor can still reach about 4000.

Figure 9:
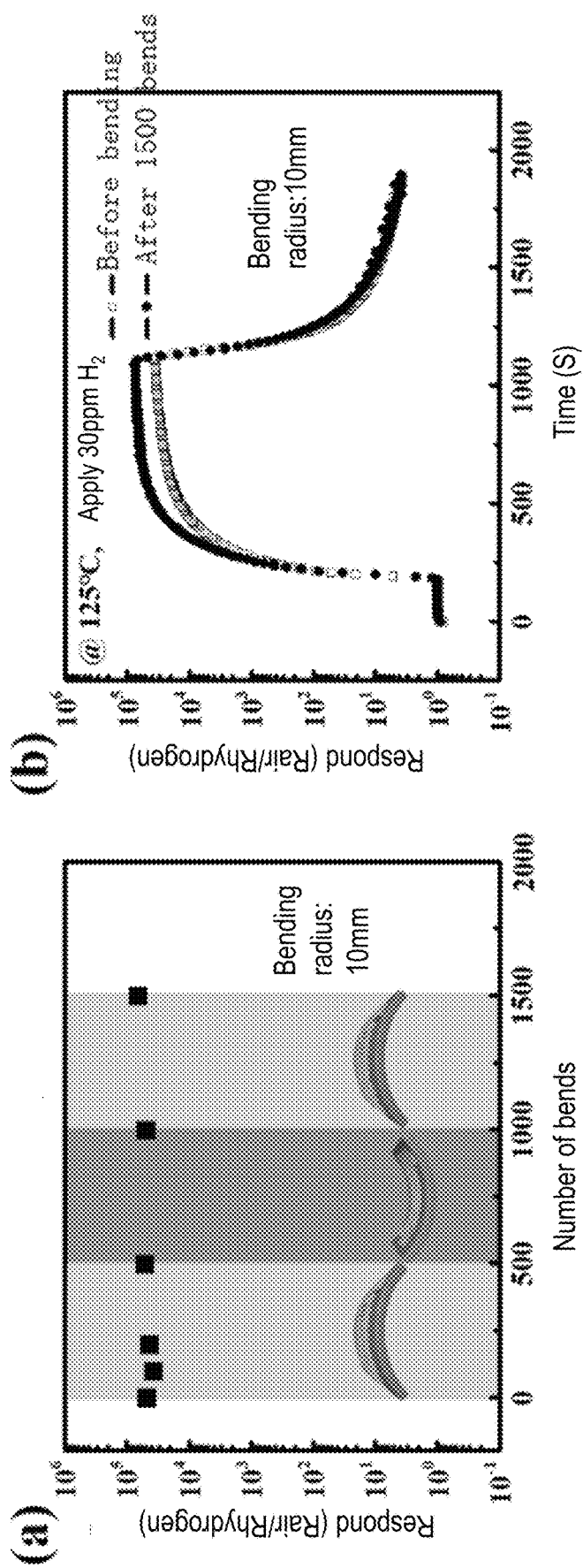
FIG. 9 shows bending stability of a Pd NPs/$SnO_2$ flexible hydrogen sensor in an example of the disclosure in (a) and a response curve to hydrogen before and after bending in (b).

FIG. 9 shows comparison diagrams of bending stability of a Pd NPs/$SnO_2$ flexible hydrogen sensor, wherein the flexible hydrogen sensor sample is subjected to convex bending and concave bending. It can be seen from (a) of FIG. 9 that after 500 times of convex bending and concave bending respectively, the flexible hydrogen sensor sample still has $10^4$ response to 30 ppm of $H_2$ at 125° C., so the flexible hydrogen sensor sample has excellent bending resistance. (b) of FIG. 9 shows comparison curves of the flexible hydrogen sensor sample to hydrogen response before and after 1500-cycle bending. It can be seen that the response curves of the both to 30 ppm of $H_2$ at 125° C. are generally consistent, so the sensor shows excellent bending stability.

Example 2

As shown in FIG. 1, a hydrogen sensor with ultra-high sensitivity based on a flexible polymer substrate includes a PET substrate, a $MO_x$ (M=Zn, X=1) film, Pd NPs and a gold interdigital electrode, and specifically includes a gold interdigital electrode, Pd NPs, a ZnO film and a PET substrate in sequence from top to bottom, wherein the coverage rate of the Pd NPs on the ZnO film is 25%.

A method for fabricating the above sensor includes the following steps:

(1) as shown in FIG. 1, the PET was selected as a substrate of the sensor and put on a cleaning rack, the cleaning rack was put in a beaker, then, the PET substrate was ultrasonically cleaned with ethanol and deionized water respectively for 5 min, and finally, the cleaned PET substrate was blow-dried with high-purity nitrogen (99.999%) for later use;

(2) a layer of ultra-thin ZnO film was deposited on the PET substrate cleaned in step (1) by ALD at a deposition temperature of 100° C., the precursor sources used were diethyl zinc and deionized water, the pulse time and cleaning time of both the diethyl zinc source and deionized water source were 0.1 s and 4 s respectively, and a ZnO film with a thickness of about 20 nm was deposited;

(3) on the basis of step (2), Pd NPs with a coverage rate of 25% were deposited by a CBD technology, wherein during deposition, the sputtering power was 35 W, the condensation distance was 65 mm, and the content of the Pd NPs was controlled by controlling the deposition time; and (4) an interdigital electrode mask was closely attached to the sample obtained after step (3) was completed, a gold with a thickness of about 200 nm was sputtered as a conductive electrode by means of magnetron sputtering, and wiring and packaging were performed to serve as a flexible sensing element for detecting hydrogen.

Example 3

As shown in FIG. 1, a hydrogen sensor with ultra-high sensitivity based on a flexible polymer substrate includes a cellophane substrate, a $MO_x$ (M=Ti, X=2) film, Pd NPs and a silver interdigital electrode, and specifically includes a silver interdigital electrode, Pd NPs, a $TiO_2$ film and a cellophane substrate in sequence from top to bottom, wherein the coverage rate of the Pd NPs on the $TiO_2$ film is 15%.

A method for fabricating the above sensor includes the following steps:

(1) as shown in FIG. 1, the cellophane was selected as a substrate of the sensor and put on a cleaning rack, the cleaning rack was put in a beaker, then, the cellophane substrate was ultrasonically cleaned with ethanol and deionized water respectively for 5 min, and finally, the cleaned cellophane substrate was blow-dried with high-purity nitrogen (99.999%) for later use;

(2) a layer of ultra-thin $TiO_2$ film was deposited on the cellophane substrate cleaned in step (1) by PEALD at a deposition temperature of 25° C., the precursor sources used were titanium tetrachloride and oxygen plasma, the pulse time and cleaning time of the titanium tetrachloride source were 0.3 s and 15 s respectively, the pulse time and cleaning time of the oxygen plasma source were 2 s and 8 s respectively, and a $TiO_2$ film with a thickness of about 10 nm was deposited;

(3) on the basis of step (2), Pd NPs with a coverage rate of 15% were deposited by a CBD technology, wherein during deposition, the sputtering power was 30 W, the condensation distance was 55 mm, and the content of the Pd NPs was controlled by controlling the deposition time; and (4) an interdigital electrode mask was closely attached to the sample obtained after step (3) was completed, a silver metal with a thickness of about 130 nm was sputtered as a conductive electrode by means of magnetron sputtering, and wiring and packaging were performed to serve as a flexible sensing element for detecting hydrogen.

Example 4

As shown in FIG. 1, a hydrogen sensor with ultra-high sensitivity based on a flexible polymer substrate includes a PANI flexible substrate, a $MO_x$ ($MO_x=Ta_2O_5$) film, Pd NPs and an aluminum interdigital electrode, and specifically includes an aluminum interdigital electrode, Pd NPs, a $Ta_2O_5$ film and a PANI flexible substrate in sequence from top to bottom, wherein the coverage rate of the Pd NPs on the $Ta_2O_5$ film is 10%.

A method for fabricating the above sensor includes the following steps:
(1) as shown in FIG. 1, the PANI flexible substrate was selected as a substrate of the sensor and put on a cleaning rack, the cleaning rack was put in a beaker, then, the PANI substrate was ultrasonically cleaned with ethanol and deionized water respectively for 5 min, and finally, the cleaned PANI substrate was blow-dried with high-purity nitrogen (99.999%) for later use;
(2) a layer of ultra-thin $Ta_2O_5$ film was deposited on the PANI substrate cleaned in step (1) by ALD at a deposition temperature of 200° C., the precursor sources used were penta(dimethylamino)tantalum and deionized water, the pulse time and cleaning time of the penta(dimethylamino)tantalum source were 1.5 s and 4 s respectively, the pulse time and cleaning time of the deionized water source were 0.1 s and 4 s respectively, and a $Ta_2O_5$ film with a thickness of about 30 nm was deposited;
(3) on the basis of step (2), Pd NPs with a coverage rate of 10% were deposited by a CBD technology, wherein during deposition, the sputtering power was 25 W, the condensation distance was 50 mm, and the content of the Pd NPs was controlled by controlling the deposition time; and
(4) an interdigital electrode mask was closely attached to the sample obtained after step (3) was completed, an aluminum metal with a thickness of about 180 nm was sputtered as a conductive electrode by means of magnetron sputtering, and wiring and packaging were performed to serve as a flexible sensing element for detecting hydrogen.

Example 5

As shown in FIG. 1, a hydrogen sensor with ultra-high sensitivity based on a flexible polymer substrate includes a PEN flexible substrate, a $MO_x$ (M=Hf, X=2) film, Pd NPs and a platinum comb electrode, and specifically includes a platinum comb electrode, Pd NPs, an $HfO_2$ film and a PEN flexible substrate in sequence from top to bottom, wherein the coverage rate of the Pd NPs on the $HfO_2$ film is 30%.

A method for fabricating the above sensor includes the following steps:
(1) as shown in FIG. 1, the PEN flexible substrate was selected as a substrate of the sensor and put on a cleaning rack, the cleaning rack was put in a beaker, then, the PEN substrate was ultrasonically cleaned with ethanol and deionized water respectively for 5 min, and finally, the cleaned PEN substrate was blow-dried with high-purity nitrogen (99.999%) for later use;
(2) a layer of ultra-thin $HfO_2$ film was deposited on the PEN substrate cleaned in step (1) by PEALD at a deposition temperature of 80° C., the precursor sources used were tetra(dimethylamino)hafnium and oxygen plasma, the pulse time and cleaning time of the tetra(dimethylamino)hafnium source were 0.1 s and 15 s respectively, the pulse time and cleaning time of the oxygen plasma source were 30 s and 25 s respectively, and an $HfO_2$ film with a thickness of about 35 nm was deposited;
(3) on the basis of step (2), Pd NPs with a coverage rate of 30% were deposited by a CBD technology, wherein during deposition, the sputtering power was 45 W, the condensation distance was 70 mm, and the content of the Pd NPs was controlled by controlling the deposition time; and
(4) an interdigital electrode mask was closely attached to the sample obtained after step (3) was completed, a platinum metal with a thickness of about 100 nm was sputtered as a conductive electrode by means of magnetron sputtering, and wiring and packaging were performed to serve as a flexible sensing element for detecting hydrogen.

Example 6

As shown in FIG. 1, a hydrogen sensor with ultra-high sensitivity based on a flexible polymer substrate includes a PEEK flexible substrate, a $MO_x$ (M=Zr, X=2) film, Pd nanoclusters and a gold comb electrode, and specifically includes a gold comb electrode, Pd nanoclusters, a $ZrO_2$ film and a PEEK flexible substrate in sequence from top to bottom, wherein the coverage rate of the Pd nanoclusters on the $ZrO_2$ film is 35%.

A method for fabricating the above sensor includes the following steps:
(1) as shown in FIG. 1, the PEEK flexible substrate was selected as a substrate of the sensor and put on a cleaning rack, the cleaning rack was put in a beaker, then, the PEEK substrate was ultrasonically cleaned with ethanol and deionized water respectively for 5 min, and finally, the cleaned PEEK substrate was blow-dried with high-purity nitrogen (99.999%) for later use;
(2) a layer of ultra-thin $ZrO_2$ film was deposited on the PEEK substrate cleaned in step (1) by ALD at a deposition temperature of 120° C., the precursor sources used were tetra(methylethylamino)zirconium and deionized water, the pulse time and cleaning time of the tetra(methylethylamino)zirconium source were 0.1 s and 4 s respectively, and a $ZrO_2$ film with a thickness of about 40 nm was deposited;
(3) on the basis of step (2), Pd NPs with a coverage rate of 35% were deposited by a CBD technology, wherein during deposition, the sputtering power was 20 W, the condensation distance was 60 mm, and the content of the Pd NPs was controlled by controlling the deposition time; and
(4) an interdigital electrode mask was closely attached to the sample obtained after step (3) was completed, a gold metal with a thickness of about 160 nm was sputtered as a conductive electrode by means of magnetron sputtering, and wiring and packaging were performed to serve as a flexible sensing element for detecting hydrogen.

The above examples are only preferred examples of the disclosure, which will help those skilled in the art to further understand the disclosure, but will not limit the disclosure in any form. It should be noted that several deformations and improvements made by those of ordinary skill in the art without departing from the concept of the disclosure fall within the protection scope of the disclosure.

What is claimed is:

1. A method for fabricating a flexible hydrogen sensor, comprising the following steps:
   a step (1): ultrasonically cleaning a flexible polymer substrate with isopropanol, ethanol and deionized water in sequence for 5 min to 10 min, and blow-drying the flexible polymer substrate with high-purity nitrogen (99.999%) for later use;
   a step (2): depositing a layer of $MO_x$ film with a thickness of 5 nm to 50 nm at a low temperature to 350° C. by thermal atomic layer deposition (ALD) or plasma-enhanced ALD (PEALD) on the flexible polymer substrate treated in the step (1);
   a step (3): depositing Pd nanoparticles (NPs) with a coverage rate of 5% to 50% on the $MO_x$ film grown in the step (2) by a cluster beam deposition (CBD) technology so as to modify the $MO_x$ film, wherein the parameters of the CBD are as follows: the pressure of a chamber is $10^{-5}$ Pa, a cluster source is filled with 100 Pa argon during deposition, the purity of the metal Pd target used is not lower than 99.9999%, the sputtering power is 20 W to 50 W, and the condensation distance is 30 mm to 80 mm;
   a step (4): depositing a metal interdigital electrode with a thickness of 100 nm to 200 nm on the $MO_x$ film loaded with Pd NPs in the step (3) as a conductive electrode by a mask, and performing wiring and packaging to obtain a $MO_x$-based flexible hydrogen sensor loaded with Pd NPs.

2. The method for fabricating a flexible hydrogen sensor according to claim 1, wherein the prepared hydrogen sensor comprises a conductive electrode layer, a sensing layer and a flexible substrate layer in sequence from top to bottom; the sensing layer is a $MO_x$ film grown by modifying ALD with Pd NPs deposited by the CBD technology; the coverage rate of the Pd NPs on the $MO_x$ film is 5% to 50%; and the conductive electrode layer is a metal interdigital electrode.

3. The method for fabricating a flexible hydrogen sensor range according to claim 1, wherein in the step (4), the conductive electrode is prepared by means of magnetron sputtering, vacuum evaporation or electron beam thermal evaporation.

4. The method for fabricating a flexible hydrogen sensor according to claim 1, wherein the thickness of the $MO_x$ film is 5 nm to 50 nm, and the M is Sn, Zn, Ti, Ta, Hf or Zr.

5. The method for fabricating a flexible hydrogen sensor according to claim 1, wherein the flexible polymer substrate comprises polyimide (PI), polyethylene terephthalate (PET), polyaniline (PANT), polyethylene naphthalate (PEN), polyether ether ketone (PEEK), polyphenylene sulfide (PPS), polymethyl methacrylate (PMMA), polydimethylsiloxane (PDMS), polycarbonate (PC), or cellophane.

* * * * *